United States Patent
Horn, Jr. et al.

(10) Patent No.: US 10,605,703 B1
(45) Date of Patent: Mar. 31, 2020

(54) PRESSURIZED GAS SUPPLY SYSTEM

(71) Applicant: Jack Delaney Horn, Jr., Friendswood, TX (US)

(72) Inventors: Jack Delaney Horn, Jr., Friendswood, TX (US); Ricky Wayne Barber, Slidell, LA (US)

(73) Assignee: Jack Delaney Horn, Jr., Friendswood, TX (US)

( * ) Notice: Subject to any disclaimer, the term of this patent is extended or adjusted under 35 U.S.C. 154(b) by 765 days.

(21) Appl. No.: 15/141,890

(22) Filed: Apr. 29, 2016

Related U.S. Application Data

(62) Division of application No. 14/135,638, filed on Dec. 20, 2013, now Pat. No. 9,335,239, which is a division of application No. 14/093,440, filed on Nov. 30, 2013, now Pat. No. 9,329,108, which is a division of application No. 12/925,089, filed on Oct. 13, 2010, now Pat. No. 8,596,340.

(51) Int. Cl.
  *F25B 21/02* (2006.01)
  *G01N 1/22* (2006.01)
  *F25B 21/04* (2006.01)

(52) U.S. Cl.
  CPC .............. *G01N 1/22* (2013.01); *F25B 21/04* (2013.01); *G01N 2001/2282* (2013.01)

(58) Field of Classification Search
  CPC ........ G01N 1/22; B01D 39/10; B01D 53/005; F25B 21/04; F25B 21/00; F25B 2321/021; F25B 2321/02; F25B 2321/025; F25B 2321/0251; F25B 2321/0252; F25B 2700/02; B60H 2001/2275; F28D 2021/0038
  USPC ............ 73/61.41, 61.46, 863.11; 374/16, 27
  See application file for complete search history.

(56) References Cited

U.S. PATENT DOCUMENTS

| | | | |
|---|---|---|---|
| 3,811,842 A | 5/1974 | Diebler et al. |
| 3,884,640 A | 5/1975 | Lock et al. |
| 4,088,458 A | 5/1978 | Jourdan |
| 4,361,539 A | 11/1982 | Weinberg et al. |
| 4,361,540 A | 11/1982 | Weinberg et al. |
| 4,397,725 A | 8/1983 | Enzer et al. |
| 4,443,407 A | 4/1984 | Weinberg et al. |

(Continued)

OTHER PUBLICATIONS www.anton-paar.com, 4 webpages relating to heating attachment for density and concentration meters, Aug, 12, 2008.

(Continued)

*Primary Examiner* — Henry T Crenshaw
*Assistant Examiner* — Kamran Tavakoldavani
(74) *Attorney, Agent, or Firm* — Keith B. Willhelm

(57) ABSTRACT

Systems for supplying pressurized air. The air feed apparatus comprises a dryer for chilling pressurized air and thereby removing humidity from the pressurized air. The dryer comprises a condenser assembly which has a condenser block and an active cooling element. The condenser block is made of metal and has an extended, serpentine passageway therein. The passageway has an inlet and outlet allowing the pressurized air to be passed through the passageway. The passageway also has a drain allowing condensed moisture to flow from the passageway. The active cooling element is mounted to the surface of the condenser block so that it can absorb heat from the condenser block.

16 Claims, 5 Drawing Sheets

(56) References Cited

U.S. PATENT DOCUMENTS

| | | | |
|---|---|---|---|
| 4,707,166 A * | 11/1987 | Khosropour | B01D 53/265 |
| | | | 55/315 |
| 4,748,531 A * | 5/1988 | Ortiz | H01H 61/002 |
| | | | 361/105 |
| 4,927,270 A | 5/1990 | Bonnard | |
| 5,253,539 A | 10/1993 | Maciel et al. | |
| 5,387,334 A | 2/1995 | Kuroda et al. | |
| 5,520,858 A | 5/1996 | Yamaguchi et al. | |
| 5,874,667 A | 2/1999 | Kasman | |
| 6,657,169 B2 * | 12/2003 | Brown | B01L 7/52 |
| | | | 219/385 |
| 6,694,747 B2 | 2/2004 | Nagai et al. | |
| 6,695,469 B2 | 2/2004 | Leonhardt | |
| 6,840,305 B2 | 1/2005 | Zheng et al. | |
| 6,989,130 B2 | 1/2006 | Deshmukh | |
| 7,090,392 B2 | 8/2006 | Leonhardt | |
| 7,378,058 B2 * | 5/2008 | Lemme | B01L 3/0203 |
| | | | 222/251 |
| 8,235,589 B1 | 8/2012 | Feller | |
| 8,596,340 B1 | 12/2013 | Horn, Jr. et al. | |
| 9,329,108 B1 | 5/2016 | Horn, Jr. et al. | |
| 9,335,239 B1 | 5/2016 | Horn, Jr. et al. | |
| 2007/0212784 A1 | 9/2007 | Okun | |
| 2010/0059126 A1 | 3/2010 | Diekmeyer et al. | |
| 2010/0269599 A1 | 10/2010 | Schroeter et al. | |
| 2012/0102973 A1 * | 5/2012 | Oh | B60H 1/00028 |
| | | | 62/3.61 |
| 2012/0174599 A1 | 7/2012 | Barnwell | |
| 2014/0137569 A1 * | 5/2014 | Parish | F25B 21/02 |
| | | | 62/3.2 |

OTHER PUBLICATIONS

Quality Control of Liquid Samples, Mettler-Toledo brochure, Dec. 2004.

* cited by examiner

PRESSURIZED GAS SUPPLY SYSTEM

FIELD OF THE INVENTION

The present invention relates to apparatus used to provide pressurized gas, and more particularly, to apparatus for providing chilled, dried pressurized gas.

BACKGROUND OF THE INVENTION

High resolution analytical instruments are capable of measuring the physical and chemical properties of materials with great accuracy. Such analysis plays an important a role in modern manufacturing processes by ensuring that starting materials meet all required specifications. The accuracy of high resolution instruments, however, can be diminished by sample related effects.

For example, it often is important to determine the density, refractive index, and other physical and chemical properties of liquids that will be used in a manufacturing process. Such properties, however, are temperature dependent. Thus, if the temperature of samples is not carefully and reproducibly controlled, even the most sophisticated instrument will provide inaccurate and inconsistent measurements.

The analytical instruments themselves are capable of maintaining the temperature of a sample, but typically have relatively limited capacity to adjust sample temperatures rapidly. It is important, therefore, that samples be introduced into an instrument at or very near the desired analytical temperature. Frequently, however, they are not. At times, they are introduced at greatly differing temperatures. When that happens the instrument may take a relatively long time to adjust the temperature of a sample. As the time required for temperature adjustment increases, so does the time required to analyze multiple samples.

For example, some analytical instruments, such as the melting/boiling point determination instrument disclosed in U.S. Pat. No. 5,874,667 to D. Kasman, utilize a metallic heater block. Samples are loaded in vials, and the vials are placed in cavities in the heater block. The temperature of the heating block, however, can take a long time to adjust if the temperature must be lowered. Moreover, sample fluids are loaded in vials, and thus the device cannot monitor the temperature of the sample directly. Vial contamination also is a significant issue. Cleaning and reusing vials may be difficult and time consuming. It also can involve added expense, as will the use of single-use vials.

Various devices, therefore, have been devised for preheating samples so that they may be introduced into an analytical instrument at or very near the desired analysis temperature. Prior art sample preheating devices typically utilize a temperature controlled fluid bath, such as a water or oil bath. Samples are loaded into vials, and the vials are immersed in the bath for a period of time before introducing the sample into an analytical instrument.

Fluid bath preheaters are widely used and are generally effective in bringing a sample to a desired temperature, but they suffer a number of deficiencies. They require the installation and maintenance of basins, fluid lines, pumps, and the like. Bath fluids, or their additives, also can present safety issues if users are accidentally exposed to them, especially since the bath may be at elevated temperatures. Moreover, bath preheaters require a relatively large supply of clean, uncontaminated vials, and because the sample is in a vial, it generally is not practical to measure the temperature of a sample directly.

The prior art, therefore, to date has failed to adequately and simultaneously address various issues relating to the performance, design, use, and fabrication of sample preheating devices. For example, it is essential that sample preheaters be able to rapidly and accurately process a series of samples, even when the samples are different or have different analysis temperatures. Thus, the temperature of samples introduced into a preheater must be easily, accurately, and quickly controlled. Any delay in adjusting the temperature of samples in the preheater will cause a corresponding delay in the ultimate analysis of samples. It also is important that issues of sample contamination and cleaning be addressed in an effective, cost efficient manner and without introducing further delay in processing different samples. Moreover, once a sample has been brought to the desired analysis temperature, its temperature must be maintained until the sample is delivered to the analytical instrument.

SUMMARY OF THE INVENTION

The subject invention provides for heater assemblies that may be used to preheat liquid samples prior to their introduction into an analytical stream, and for heat sink assemblies and rinse systems incorporated into such sample preheaters. The novel sample preheaters comprise a heat sink assembly having a metallic heater block which preferably is fabricated from at least two parts. A heating element is in thermal communication with the heater block and is adapted to transfer heat to the heater block.

The heater block has a basin for receiving a liquid sample and allowing heat to be transmitted from the heater block to the sample. There is a drain at the lower end of the basin allowing sample in the basin to flow out of the basin. A passageway extends through the heater block from the drain to an exterior surface of the heater block and provides a conduit for sample flowing from the drain. The passageway preferably provides an extended, indirect conduit for conveying sample fluids from the basin.

A temperature sensor is mounted in a cavity in the heater block and extends into the basin and is adapted to measure the temperature of liquid in the basin. A temperature sensor is mounted in a cavity in the heater block and is adapted to measure the temperature of the heat sink heater block.

Preferred embodiments of the novel heat sink assemblies also comprise a cooling element, such as a Peltier cooler, in thermal communication with the heater block which is adapted to transfer heat from the heater block.

The novel heater assemblies also preferably comprise a rinse system for introducing solvent into the sample basin. Preferably the rinse system incorporates a wash ring constructed in accordance with other aspects of the subject invention. The novel wash ring is mounted on top of the heater block around the basin. The wash ring and heater block assembly define a manifold and a port which provides liquid communication between the manifold and the basin. Preferred embodiments define an annular manifold and an annular port for directing liquid from the manifold in a laminar sheet flowing generally along the surface of the basin, one or more ports for directing liquid from the manifold in a generally radial stream into the basin, or both types of ports. Other preferred embodiments include a second passageway extending through the heater block to the manifold. The second passageway provides a conduit through the body for introducing rinse liquid into the manifold.

The rinse systems preferably are driven by pressurized air which has been passed through a dryer to remove excess moisture from the air. Preferably, the dryer comprises a condenser assembly for removing humidity from pressurized air which has been constructed in accordance with other aspects of the subject invention. The novel condenser assemblies comprise a metallic condenser block which preferably is fabricated from at least two parts. The condenser block has a passageway which has an inlet and outlet, thus allowing pressurized air to be passed through the condenser block. The passageway defines an extended, serpentine course so as to increase the residence time of air passing through the condenser block and to allow more efficient cooling of the air. The condenser block also has a drain which allows moisture condensed in the block to flow therefrom.

A cooling element is mounted to the surface of the condenser block for absorbing to heat from the condenser block. The cooling element preferably is a Peltier cooler. The condenser assembly also preferably includes a regulator in fluid communication with the condenser block for reducing the pressure of air discharged from the condenser.

It will be appreciated that the novel heater assemblies allow for effective, efficient, rapid, and easy control over the temperature of the heat sink assembly and, therefore, of samples loaded therein. Moreover, they allow for rapid and easy processing of different samples with a minimum of downtime.

Other aspects and embodiments of the subject invention provide an air feed apparatus for supplying pressurized air. The air feed apparatus comprises a dryer for chilling pressurized air and thereby removing humidity from the pressurized air. The dryer comprises a condenser assembly which has a condenser block and an active cooling element. The condenser block is made of metal and has an extended, serpentine passageway therein. The passageway has an inlet and outlet allowing the pressurized air to be passed through the passageway. The passageway also has a drain allowing condensed moisture to flow from the passageway. The active cooling element is mounted to the surface of the condenser block so that it can absorb heat from the condenser block.

Another aspect and embodiment provides air feed apparatus where the cooling element is a Peltier cooler mounted to the condenser block.

Alternate aspects and embodiments are directed to air feed apparatus where the condenser assembly comprises a regulator in fluid communication with the block outlet for reducing the pressure of air discharged from the condenser block.

Still other aspects and embodiments provide air feed apparatus where the condenser block is assembled from at least two parts.

Further aspects and embodiments provide air feed apparatus where the air feed system comprises a moisture sensor adapted to measure the moisture content of air passing through the air feed system or where the air feed system comprises a moisture sensor upstream of the inlet of the condenser block and a moisture sensor downstream of the outlet of the condenser block.

DESCRIPTION OF ILLUSTRATIVE EMBODIMENTS

Figure 1:
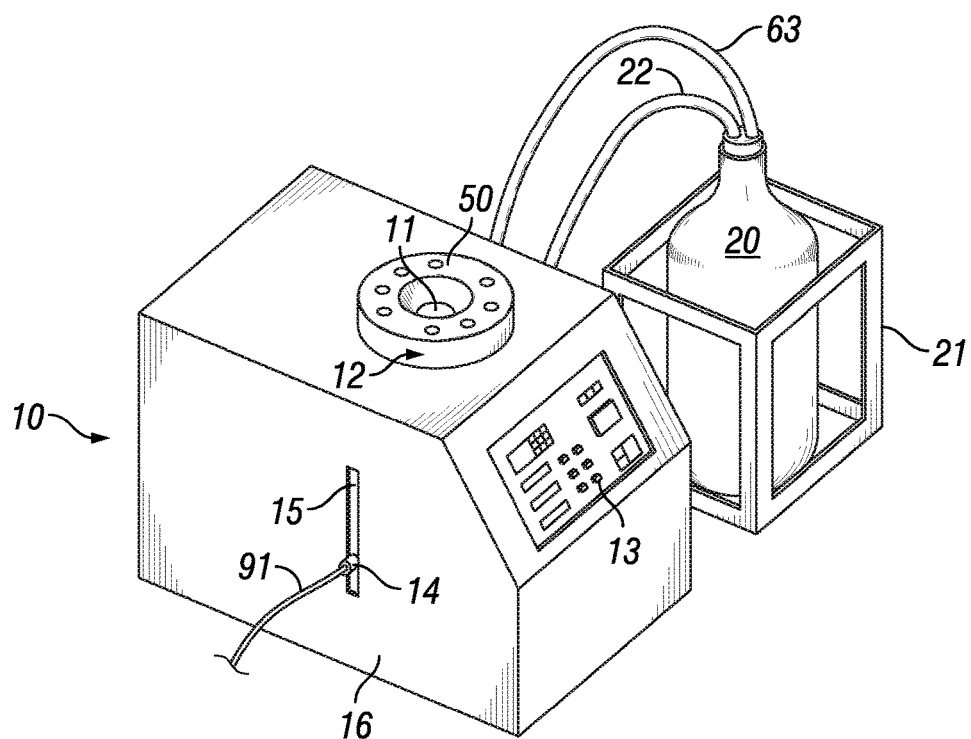
FIG. 1 is a perspective view taken generally above, in front of, and to one side of a preferred heater assembly 10 for preheating sample liquids which is constructed in accordance with the subject invention.

The heater assemblies of the subject invention, such as the preferred embodiment 10 and its various components illustrated in FIGS. 1-10, are intended for use in preheating liquid samples which will be introduced into an analytical instrument or other analytical streams. For example, as shown generally in the preferred sample preheater 10 shown in FIG. 1, liquid samples may be introduced into a sample basin 11 in a heat sink assembly 12 for preheating. Desired temperatures and other process parameters and operations may be set via a control panel 13. Once it has been preheated, the sample is withdrawn from sample basin 11 and fed into an analytical instrument, such as instrument 90 shown schematically in FIG. 2, via internal drains, passageways, and conduits (not shown in FIG. 1) and a sample discharge connection 14. Sample discharge connection 14 preferably is a standard threaded connection which is compatible with vacuum feed lines commonly used in analytical instruments so that sample preheater 10 may be easily and rapidly connected to instrument 90 via a sample conduit 91. It also will be noted that discharge connection 14 is slidably mounted in a slot 15 in cabinet 16 so that it may be positioned to provide the most effective connection to an analytical instrument.

It typically is necessary to run many different samples for analysis. Thus, sample preheater 10 also includes a rinse system for introducing a wash solvent into heat sink 12 to clear sample basin 11, and the various passageways and lines flowing from sample basin 11, of any residue from prior samples or contamination before introducing a new sample. The rinse system includes a solvent reservoir 20 which is carried in a stand 21. Pressurized air is introduced into the reservoir 20 via an air feed line 63 and may be used to drive solvent from reservoir 20 through a solvent feed line 22 and into sample basin 11 via various internal conduits and passageways (not shown) and a wash ring 50.

Thus, it will be appreciated that the novel heater assemblies comprise a heat sink for heating a liquid sample. In accordance with the invention, the heat sink comprises a metallic heater block which defines a basin for receiving a liquid sample and allows heat to be transmitted from the heater block to the liquid. The basin has a drain at its lower end which allows liquid to flow from the basin.

Figure 5:
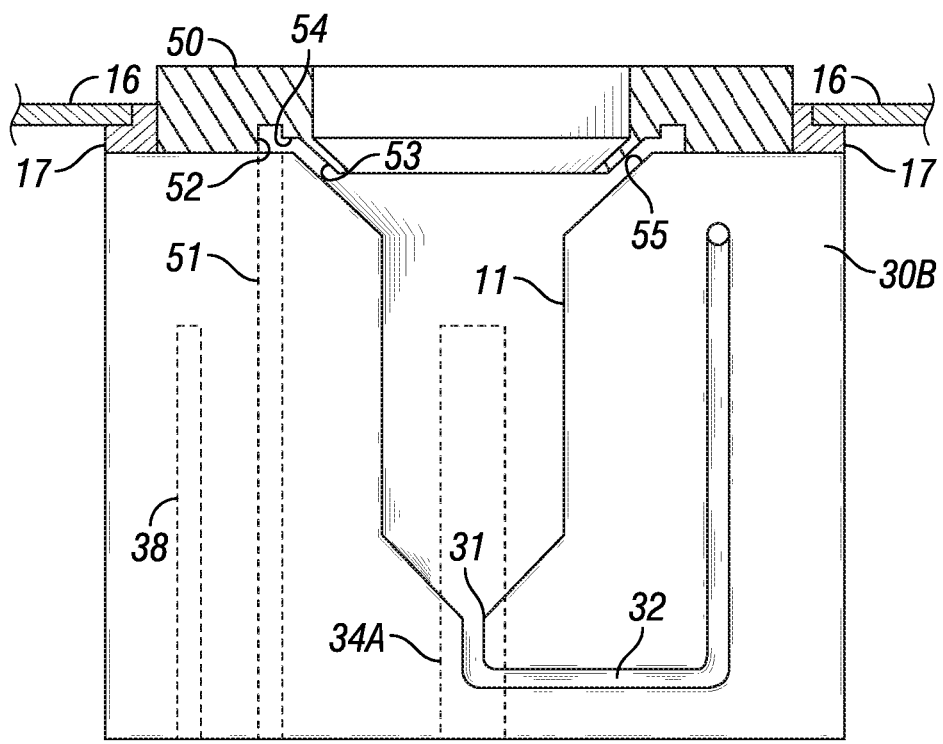
FIG. 5 is a cross-sectional view taken generally along line 5-5 of FIG. 4 showing various components of the preferred heat sink 12 shown in FIGS. 3 and 4.
Figure 6:
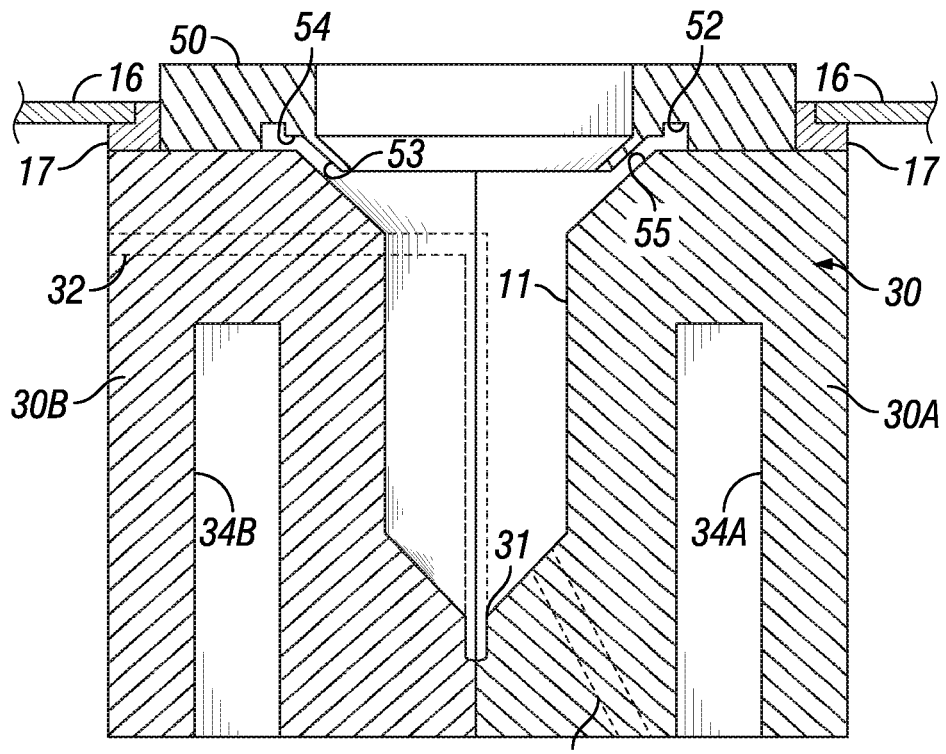
FIG. 6 is a cross-sectional view taken generally along line 6-6 of FIG. 3 showing various components of the preferred heat sink 12 shown in FIGS. 3 and 4.

For example, as seen best in FIGS. 5 and 6, sample basin 11 is defined in heater block 30. Sample basin 11 allows heat to be transferred from heater block 30 to the liquid quickly and efficiently. It is generally cylindrically shaped. Its upper end is flared outward to facilitate introduction of a sample. Its lower portion is tapered inwardly toward a drain 31. Other configurations, however, may be used for the sample basin in the novel heat sinks. The precise configuration and dimensions thereof are largely a matter of preference determined in accordance with desired capacity levels and efficiency in transferring heat.

The novel heat sink assemblies also comprise a passageway extending through the heater block from the drain to an exterior surface of the heater block. The passageway provides a conduit through the heater block for liquid flowing from the drain with minimal heat loss. Preferably, the passageway provides an extended, indirect conduit for increasing the residence time of sample fluids conveyed from the sample basin and out of the heater block. For example, as may be seen in FIG. 5, sample passageway 32 is provided in heater block 30. It defines an extended course through heater block 30. More specifically, passageway 32 has a first section extending generally downward from drain 31. A second portion of passageway 32 then extends generally horizontally from the first portion, and a third section extends generally upward from the second portion. Passageway 32 has a final, fourth section extending generally horizontally (and into the plane of FIG. 5) from the third portion to the exterior surface of heater block 30. Other configurations for the sample passageway, however, may be devised and used if desired Sample fluid flowing through passageway 32 then is discharged into a sample discharge line 33 (shown in FIGS. 3-4) which is secured to heater block 30 via suitable connections, fittings, and the like. The downstream end (shown schematically in FIG. 2) of sample discharge line 33 is connected to sample discharge connection 14 which is mounted on cabinet 16. Discharge connection 14 provides a connection for sample conduit 91 of analytical instrument 90. Sample discharge line 33 preferably is fabricated from plastics which are poor heat conductors, such a polytetrafluoroethylene, and preferably is further provided with an insulating sheath, thereby minimizing the heat loss of sample fluid flowing from heater block 30.

It will be appreciated that by providing an extended, indirect conduit for fluid drained from the basin, along with insulative or insulated sample discharge lines, the temperature of the sample is maintained as it flows toward an analytical instrument. Cooling of the fluid is minimized and, therefore, a sample may be introduced into the analytical instrument at or very near the desired analysis temperature. This in turn ensures that the amount of time required for temperature equilibration in the analytical instrument is minimized and allows for samples to be analyzed by the instrument at a faster rate.

The heater block is fabricated from metal to ensure rapid and efficient transfer of heat from a heat source to sample fluids in the basin. Aluminum is preferred as it is lightweight and relatively easy to cast and mill. Other metals may be used, however, and may be preferred depending on the application. For example, if the fluids to be analyzed are corrosive, stainless steel and other more corrosion resistant metals may be preferred. In that event, chemically resistant coatings also may be applied to the block in those areas exposed to corrosive liquid.

The heater block preferably is assembled from at least two parts. Those parts, in turn, preferably are releasably connected to facilitate assembly and disassembly of the heater block. For example, as may be seen in FIGS. 3 and 4, heater block 30 is fabricated from two halves 30a and 30b. A unitary heater block may be used, but it will be appreciated that fabrication of the various passageways, chambers and other features of the heater block is simplified if it is assembled from at least two parts. For example, solvent passageway 32 seen in FIGS. 5 and 6 may be formed by milling a groove in one or both mating surfaces of heater block halves 30a and 30b. More complex passageways may be provided more easily, therefore, as compared to drilling in or casting a unitary block. Generally, two heater block halves of more or less equal overall dimensions will allow easy fabrication of the sample passageway and other features of the heater block, but more parts may be used if desired.

Heater block halves 30a and 30b are releasably connected to each other via countersunk nuts and bolts or other conventional fasteners such as screws, clamps, and the like. Servicing of the block may be facilitated if it can be disassembled. Heater block halves 30a and 30b, however, also may be more or less permanently affixed to each other by adhesives, welding, and the like. It also will be appreciated that thermally conductive caulk, o-rings, and the like (not shown) preferably are employed to enhance thermal conduction and to provide a seal between the heater block halves 30a and 30b.

Figure 4:
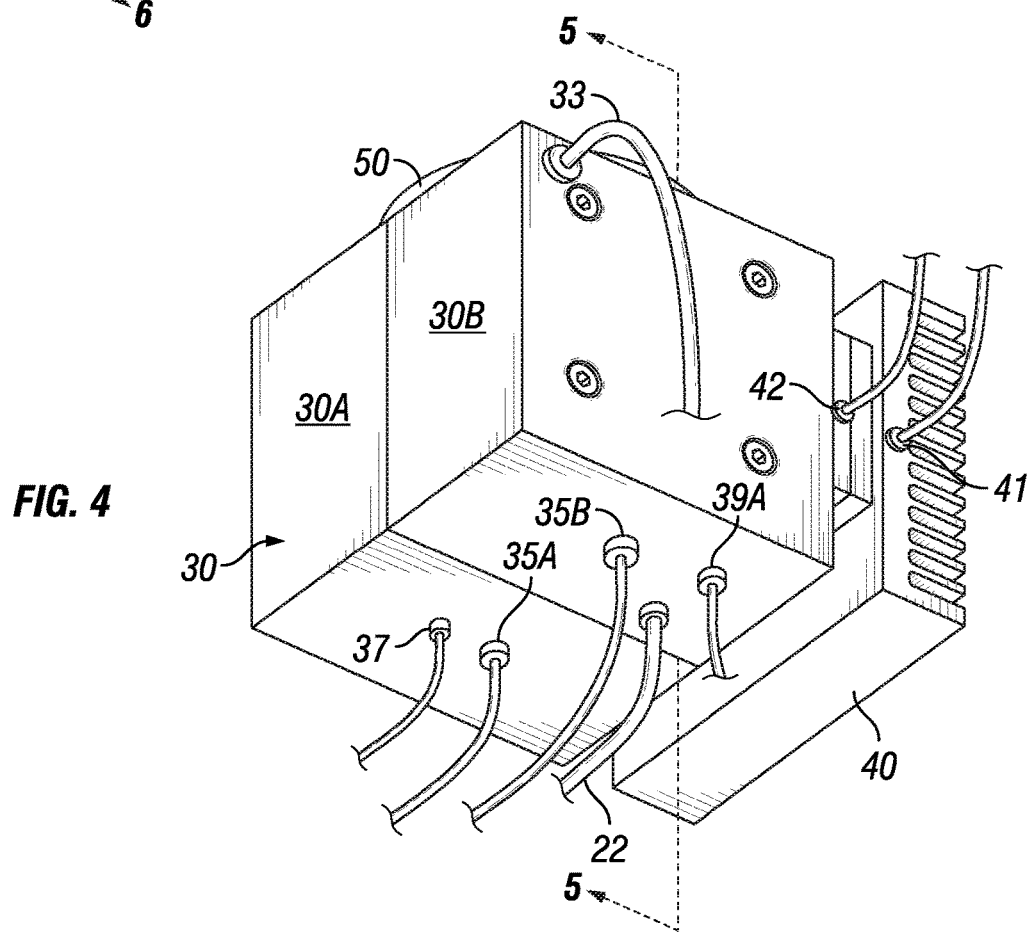
FIG. 4 is a perspective view taken generally below, in front of, and to one side of the preferred heat sink 12 shown in FIG. 3.

The novel heater assemblies comprise a heating element in thermal communication with the heater block and which is adapted to transfer heat to the heater block. Thus, the heater block preferably has a cavity which is adapted to receive a heating element. For example, as shown in FIGS. 5 and 6, heater block 30 has a pair of generally cylindrical cavities 34a and 34b. Heating elements 35a and 35b, which may be seen in part in FIG. 4, are carried therein. Cavities 34 are sized to closely fit heating elements 35 so as to facilitate efficient transfer of heat to block 30. Thermally conductive caulk also preferably is applied in mounting heating elements 35 in cavities 34 to further enhance heat transfer. A pair of heating elements is used to ensure more uniform heat flow into the block. More or fewer heating elements may be used, however, as desired.

Heating elements 35 preferably are sealed, tubular electrical resistance heaters. Such elements are preferred because they are compact, reliable, inexpensive, and may be controlled easily. Other types of heating elements may be used, however, and it will be appreciated that the block cavity will be configured accordingly. Alternately, a heating element may be mounted to the exterior of the block or in any number of ways which allow efficient and effective flow of heat to the block.

Figure 3:
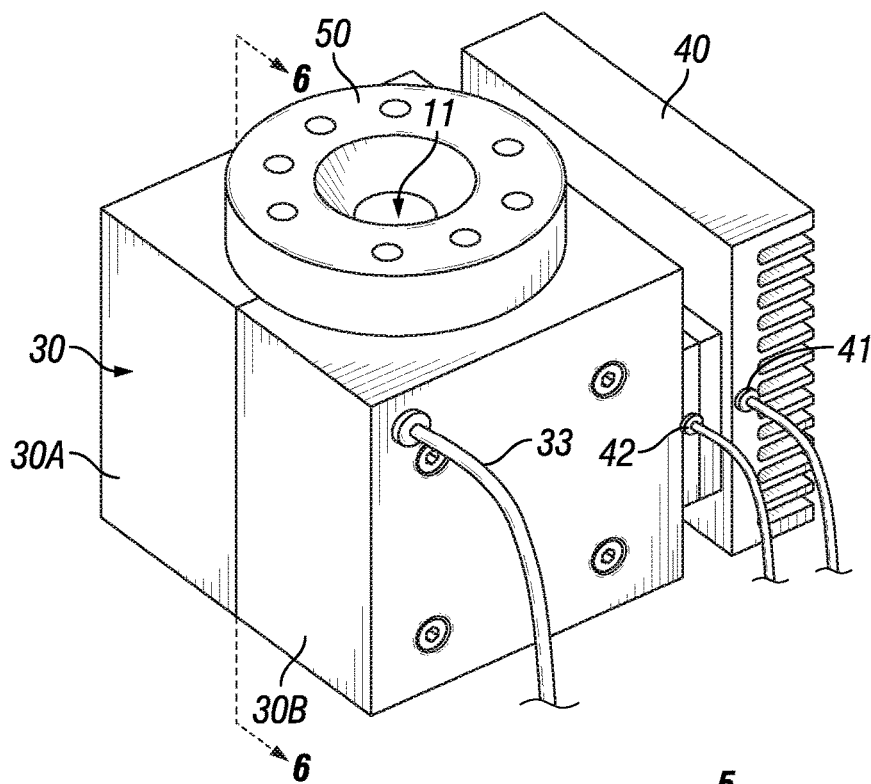
FIG. 3 is a perspective view taken generally above, in front of, and to one side of a preferred heat sink assembly 12 of the subject invention, which heat sink 12 is incorporated into the sample preheater 10 shown in FIG. 1.

The novel heat sink and heater assemblies preferably comprise a cooling element in thermal communication with the heater block which is adapted to transfer heat from the heater block. For example, as seen in FIGS. 3 and 4, heat sink 12 has cooling element 40 which is mounted to the surface of metallic heater block 30. Cooling element 40 is able to absorb heat from heater block 30, thus allowing more rapid cooling of heater block 30 in the event that a lower sampling temperature is desired.

Cooling element 40 preferably is a Peltier cooler. Peltier coolers are based on the reverse thermoelectric effect and are able to transfer heat from one side (the cold side) of a body to the other (the hot side) when current is applied. While they are not particularly energy efficient, Peltier coolers are compact and light and contain no coolant, and thus are preferred for use with the novel heat sinks and sample preheaters. Other cooling elements, such as Carnot refrigerators, may be used if desired, or chilled air, water, or other fluids may be circulated in a controlled fashion through or around the block.

Peltier cooler 40 preferably has sensors, such as thermocouple sensors 41 and 42, for sensing the temperature of the hot and cold sides of cooler 40. Temperature sensors 41 and 42, and other temperature sensors incorporated into the novel heater assemblies, preferably are mounted with a thermally conductive caulk to enhance thermal communication with the sensor. Preferably, the surface of heater block 30 is countersunk so that the cold side of Peltier cooler 40 is able to nest therein. This will provide greater contact and ultimately facilitate heat transfer between heater block 30 and the cold side of cooler 40. A thermally conductive caulk also may be applied in those contact areas to further enhance heat transfer.

It will be appreciated that by incorporating both heating and cooling elements the temperature of the novel heat sink assemblies may be adjusted as required more rapidly. Thus, the novel heater assemblies are capable of more rapidly preparing a series of samples for analysis and ultimately of increasing the rate at which they are analyzed.

The novel heater assemblies also comprise a pair of temperature sensors mounted in cavities in the heater block. One sensor extends into the sample basin and is adapted to measure the temperature of liquid in the basin. The other sensor extends into the heater block and is adapted to measure the temperature of the heater block. The sensors allow for measurement and ultimately control of the temperature in the sample basin and block.

For example, as may be seen in FIG. 6, heater block 30 has a cavity 36. Temperature sensor 37, which may be seen in part in FIG. 4, is mounted in cavity 36 and extends into basin 11 and, therefore, into any sample fluid which is present in the basin. Heater block 30 has a cavity 38 as may be seen in FIG. 5. Temperature sensor 39a, which may be seen in part in FIG. 4, is mounted in cavity 38 and allows measurement of the heat sink temperature.

Sensors 37 and 39a are thermocouple temperature sensors. Such sensors are preferred because they are compact, inexpensive, and reliable. Other types of temperature sensors may be used, however, and it will be appreciated that the corresponding block cavities will be configured accordingly. Likewise, the sensors may be mounted in various ways which will allow them to measure the temperature of the heater block and sample.

Additional sensors also may be provided for monitoring the temperature of the block and such sensors can provide useful feedback for monitoring or diagnosing conditions in the block. For example, thermocouple sensors 39b and 39c (shown schematically in FIG. 2) may be mounted on the surface of each heater block half 30a and 30b. Sensors 39b and 39c are able to provide input useful in alerting a user of possible overheating, or in automatically shutting off heating elements 35 to prevent overheating of block 30 (and any sample therein) in the event that sensor 39a fails. Sensors 39b and 39c also could provide additional input useful in diagnosing failures of heating elements 35.

As noted, the novel heater assemblies preferably comprise a rinse system for introducing a wash solvent into the heat sink to clear the sample basin, passageways, and lines of any prior samples or contamination before introducing a new sample. The rinse system comprises a solvent reservoir which is in liquid communication with and provides solvent to a novel wash ring which in turn discharges solvent into the sample basin. More particularly, the wash ring is mounted on top of the heater block around the basin and those two components define a manifold and a port for introducing solvent into the basin.

Figure 2:
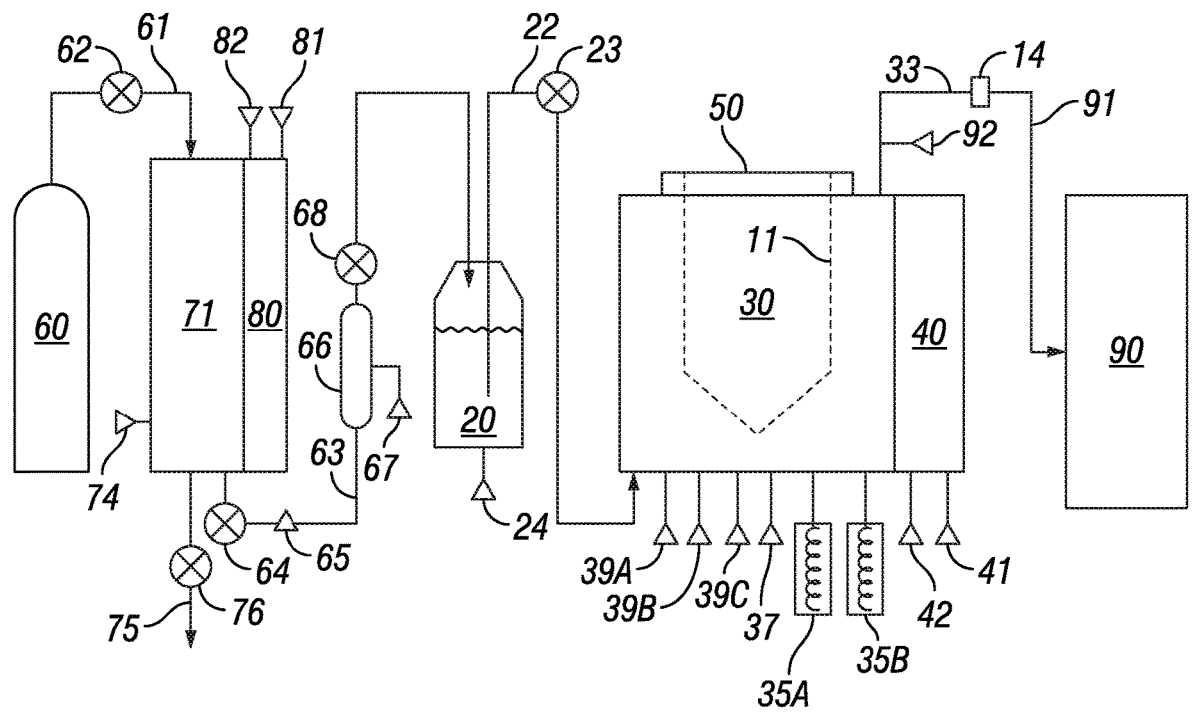
FIG. 2 is a schematic diagram showing various components of the preferred sample preheater 10 shown in FIG. 1.

For example, as shown in FIG. 1 and schematically in FIG. 2, sample preheater 10 is provided with solvent reservoir 20. Solvent from reservoir 20 flows through solvent feed line 22 into sample preheater 10. More particularly, as may be seen best in FIGS. 4 and 5, solvent feed line 22 is connected, via connections, fittings, and the like, to heater block 30. Solvent from feed line 22 discharges into a passageway 51 provided in heater block 30 and, ultimately, into wash ring 50. It will be appreciated that passing solvent through passageway 51 allows the solvent to be warmed which in turn increases its ability to dissolve and remove contaminants.

It also will be appreciated that preheater 10 may be provided with additional reservoirs similar to reservoir 20. Such additional reservoirs may be used to provide additional solvent capacity. More importantly, however, an additional reservoir may allow for uninterrupted flow of solvent during rinsing operations. Additional reservoirs also may be provided to allow for the use of different solvents.

Figure 7:
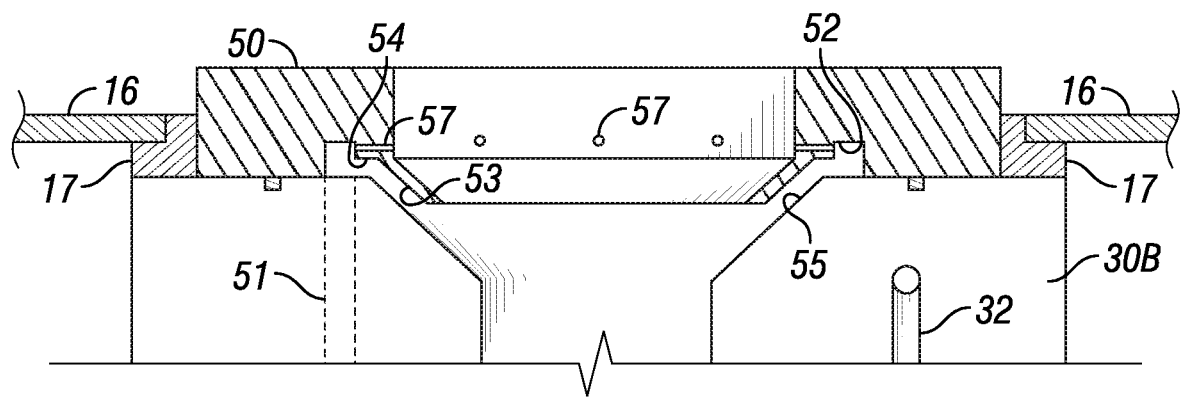
FIG. 7 is an enlarged view of the upper portion of FIG. 5.
Figure 8:
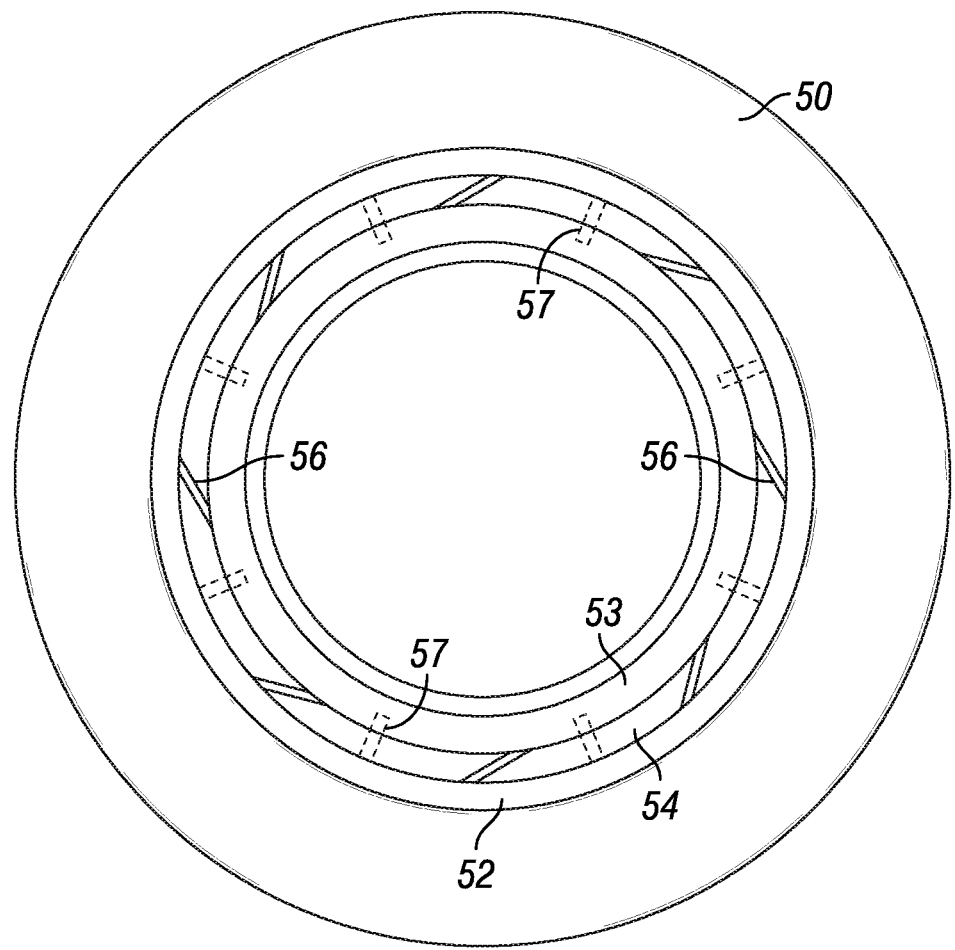
FIG. 8 is a bottom plan view of a wash ring 50 shown in FIGS. 5-7.

Wash ring 50 is seen best in FIGS. 7-8. As may be seen therefrom, wash ring 50 is releasably mounted on top of heater block 30 by screws (not shown). Nuts and bolts and other fasteners, however, may be used, and releasable fasteners are preferred so that wash ring 50 may be disassembled in the event cleaning or other service is required. If desired, however, wash ring 50 may be secured to heater block 30 via adhesives, welding and the like. An o-ring is provided between wash ring 50 and heater block 30 to provide sealing. Caulk or other sealing means and materials, however, may be used as desired.

In accordance with other aspects of the subject invention, the wash ring and heater block assembly preferably define an annular manifold and a port for directing liquid from the manifold into the basin in a laminar sheet flowing generally along the surface of the basin. Preferably, ports also are provided for directing liquid from the manifold into the basin in a series of generally radial streams.

For example, wash ring 50 has an annular groove 52 in its lower surface which is situated above solvent passageway 51, thus forming a manifold for distributing solvent introduced into the wash ring via solvent passageway 51. It will be appreciated, however, that heater block 30 may be provided with additional, suitably disposed solvent passageways, such as a passageway located 180° from passageway 51, and such additional passageways may allow for more effective distribution of solvent through manifold 52.

The inner, lower end of wash ring 50 is tapered inwardly and fits generally within the upper, flared end of sample basin 11. Surface 53 of that taper and adjacent surface 54 define a narrow annular gap 55 between wash ring 50 and the opposing surface of sample basin 11. That gap 55 serves as a port which tends to encourage a laminar flow of solvent from manifold 52 into sample basin 11 generally along the surface thereof. Angled grooves 56 as shown in FIG. 8 preferably are provided in surface 54 to impart angular momentum to the laminar flow, that is, to encourage a swirling, laminar flow into basin 11.

Wash ring also preferably has a plurality of ports 57 extending radially inward from the manifold 52 to the interior of the rings. Such ports are adapted to provide a series of streams directed into sample basin 11 in a generally radially inward direction, that is, toward the opposing side of basin 11. The streams may be directed generally upward or downward as desired to ensure effective rinsing of all surfaces of basin 11.

It will be appreciated that the precise shape and dimensions of the manifold and of the various ports may vary within the scope of the subject invention. For example, gap extends continuously around wash ring 50 and provides an annular laminar flow extending around the entire circumference of basin 11. Gap 55, however, may be discontinuous and provide multiple, discreet laminar flows if desired. Likewise, ports 57 may be sized to provide relatively intact streams or to provide various degrees of "misting" as required. In general, the various ports may be configured to provide a wide range of flow characteristics for solvent being introduced into the basin, such as profile, rate, and pressure, so as to provide the most effective rinsing of contaminants. Optimal flow characteristics generally will depend on a number of factors, including the size and shape of the sample basin, the solvent being used, and the amount and nature of the contaminants that will be encountered.

It will be appreciated that a unitary wash ring which, together with the upper surfaces of the heater block, cooperatively defines the various manifolds and ports as described above is preferred. That design allows the manifold and ports to be fabricated with precision and relative ease. The novel wash rings, however, may be fabricated from two parts, with the component parts defining the annular manifold and laminar flow port. In such embodiments, the second part of the wash ring would serve the same purpose as the upper surfaces of the heater block as described above. The wash ring also could be fabricated from more than two parts, or may include parts that might otherwise be considered part of the heater block consistent with the goal of defining the described manifold and ports.

Moreover, the novel wash rings, though exemplified herein as part of the novel heat sink assemblies, may be used with other heat sinks that have a sample basin. They are not limited in their application to the novel heat sink assemblies specifically described herein.

Solvent preferably is pumped from the reservoir via pressurized air, preferably after it has passed through a dryer to remove humidity from the air. For example, as shown schematically in FIG. 2, a pressurized air supply 60, such as a tank or pump, may be used. Air supply 60 supplies pressurized air to a condenser assembly 70 (shown in FIG. 10) via an air feed line 61. Preferably, air feed line 61 includes suitable devices to control or condition the flow of air introduced into condenser assembly 70. For example, air regulator 62 may be provided to set the pressure at which air flows to condenser assembly 70. A filter also preferably is provided, either as a separate component or as part of air regulator 62. If desired, a shut-off valve, such as a solenoid valve, also could be provided in air feed line 61.

Figure 9:
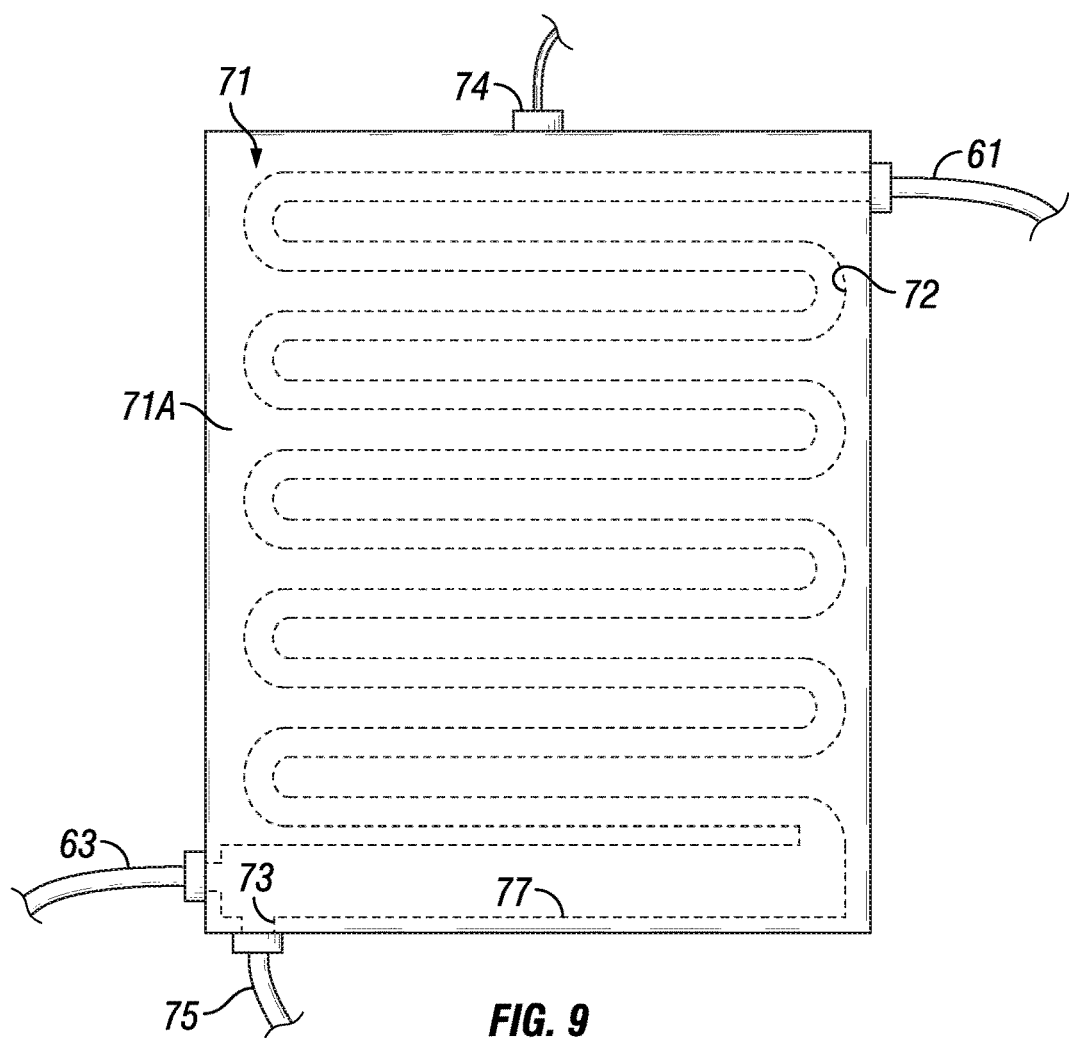
FIG. 9 is a end plan view of a preferred condenser assembly 70 incorporated into the novel sample preheater 10.
Figure 10:
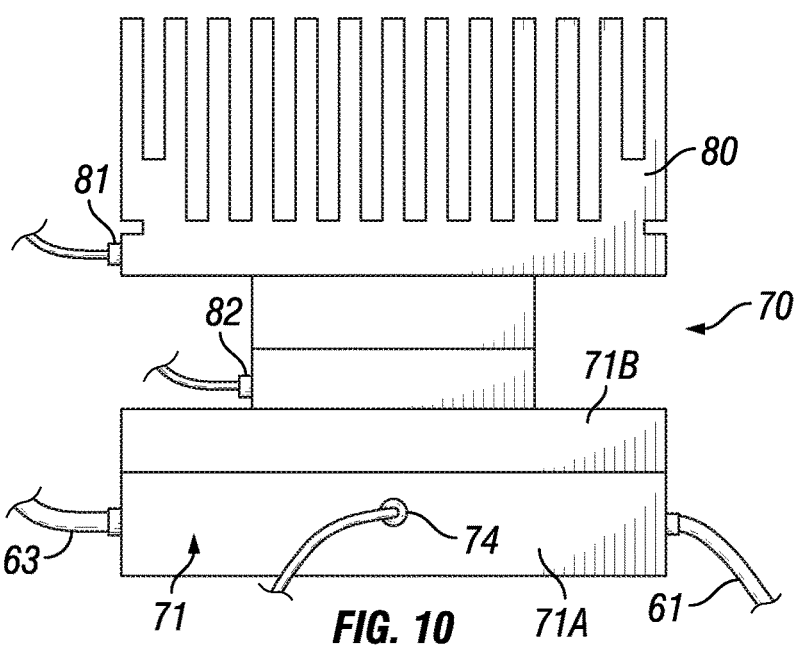
FIG. 10 is top plan view of condenser assembly 70 shown in FIG. 9.

As shown in FIG. 10, condenser assembly 70 includes a condenser block 71 and a cooling element 80. Condenser block 71, as shown in FIG. 9, has an extended, serpentine passageway 72 passing therethrough. Passageway 72 provides a conduit and allows heat from air passing therethrough to be rapidly and efficiently transferred to condenser block 71. The extended, serpentine course of passageway 72 increases the residence time of air in condenser block 71 allowing a corresponding increase in heat transfer. Such heat transfer typically will cause condensation of moisture in the air, so it will be appreciated that passageway 72 is configured to allow water to flow out of condenser block 71 via drain 73. Preferably, block 71 also is provided with a collection well 77 to allow some accumulation of water therein. The invention is not limited, however, to the passageway 72, drain 73, and well 77 as shown. It will be appreciated the precise dimensions and layout of a suitable passageway, drain, and collection well may be varied considerably consistent with the goals of allowing efficient condensation, collection, and evacuation of moisture.

Cooling element 80 is mounted to the surface of condenser block 71 so that it is able to rapidly and efficiently absorb heat from condenser block 71, thus ensuring more efficient removal of moisture from the air passing through condenser block 71. Cooling element 80 preferably is a Peltier cooler which has sensors, such as thermocouple temperature sensors 81 and 82, for sensing the temperature of the hot and cold sides of cooler 80. Preferably, the cold side of Peltier cooler 80 is countersunk into condenser block 71 to increase the areas of contact and to facilitate heat transfer therebetween. A thermally conductive caulk also may be applied in those contact areas to further enhance heat transfer. For the same reasons as discussed above in reference to heat sink cooler 40, Peltier coolers are preferred for use in the condenser assembly of the novel sample preheaters. Other cooling elements or means of cooling block 71, such as Carnot refrigerators, may be used if desired, or chilled fluids may be circulated in a controlled fashion through or around the block. Condenser block 71 preferably is fabricated from metal to ensure rapid and efficient transfer of heat. Aluminum is preferred as it is lightweight and relatively easy to mill, but other metals may be used if desired. As with heater block 30, condenser block 71 also is preferably assembled from at least two, releasably connected parts. For example, condenser block 71 is fabricated from two halves 71a and 71b. A unitary body may be used, but fabrication of the various passageways, chambers and other features of the condenser block 71 is simplified by the use of at least two parts. Additional sections may be used if desired.

Block halves 71a and 71b are releasably connected to each other via, for example, nuts and bolts, screws, clamps, and other conventional fasteners (not shown). Servicing of the condenser block may be facilitated if it can be disassembled. Block halves 71a and 71b, however, also may be more or less permanently affixed to each other by adhesives, welding, and the like. It also will be appreciated that caulk, o-rings, and the like (not shown) preferably are employed to provide a seal between the block halves 71a and 71b.

Block half 71b is provided with a countersunk area designed to accommodate the cold side of Peltier cooler 80. As shown in FIGS. 9-10 and schematically in FIG. 2, condenser block may be provided with a temperature sensor, such as thermocouple temperature sensor 74, for monitoring the temperature of condenser block 71. Condenser block 71 also is provided with a drain line 75 running from drain 73. A valve, such as solenoid valve 76, preferably is incorporated into drain line 75 to control the flow of water from condenser block 71.

As shown schematically in FIG. 2, air feed line 63 runs from condenser block 71 to solvent reservoir 20. An air regulator, such as electronic regulator 64, and a pressure sensor, such as solid state pressure transducer-transmitter 65, preferably are incorporated into air feed line 63 to control the flow of and pressure of air from condenser block 71. Air tank 66 preferably is provided in air feed line 63 downstream of regulator 64 and sensor 65 to provide a buffer and to ensure that air is introduced into reservoir 20 at a more uniform rate. A moisture sensor, such as relative humidity sensor-transmitter 67, also may be provided in air reservoir 66 to monitor the moisture content of air introduced into reservoir 20. A valve, such as a solenoid valve 68, preferably is provided downstream of air tank 66 to provide additional control over air flow into reservoir 20.

Additional moisture sensors may be provided if desired to provide additional monitoring and control over the relative humidity of air introduced into solvent reservoir 20. For example, a moisture sensor may be provided in collection well 77 to monitor the humidity of air in condenser block 71. A moisture sensor also may be provided upstream of the condenser assembly 70 to monitor the humidity of air introduced therein.

Air feed line 63 introduces air into the upper portion of solvent reservoir 20, which in turn causes solvent to flow from reservoir 20 via solvent feed line 22. A valve, such as solenoid valve 23, preferably is incorporated into solvent feed line 22 to control the flow of solvent from reservoir 20. Preferably, the solvent rinse system includes means for monitoring the amount of solvent in the reservoir. For example, as shown schematically in FIG. 2, solvent reservoir 20 may be supported over a load cell 24 mounted in stand 21. Load cell 24 may be used to measure the weight of the reservoir 20 and, indirectly, the amount of solvent in reservoir 20.

Rinse solvent, after it is introduced into sample basin 11, is withdrawn (via passageway 32 and sample discharge line 33) by a vacuum applied through sample conduit 91 of analytical instrument 90. Thus, sample discharge line 33 preferably is provided with means for detecting the presence of a vacuum therein. For example, as shown schematically in FIG. 2, vacuum interlock switch 92 is provided in sample discharge line 33. Interlock switch 92 is activated upon detection of a vacuum in line 33. It may be utilized to enable an override function to preclude or shut down a rinse operation in the event that no vacuum is detected, thus avoiding any unintentional overflow of rinse solvent from sample basin 11 if instrument 90 is disconnected or is not drawing fluids.

It also will be appreciated that the condenser assembly 70 may be used as a source of pressurized, chilled air for cooling heater block 30. That is, heater block 30 may be provided with serpentine passageways similar to those in condenser block 71 and chilled air from condenser assembly 70 may be circulated therein in a controlled fashion. Air flowing through condenser assembly 70 may be at relatively high pressures. Thus, regulator 64 preferably is set to create a pressure drop before air is fed into heater block 30. Alternately, a control device, such as an expansion valve or a regulator, may be provided in a feed line to heater block 30 to create a pressure drop. In either event, allowing its expansion will further cool air introduced into heater block 30 and enhance its cooling effect. While Peltier cooler 40 will provide more rapid cooling of heater block 30, using chilled air from condenser assembly 70 obviates the need for an additional cooling element and can reduce the power requirements for sample preheater 10.

Moreover, the novel condenser assemblies, though exemplified herein as applied to the novel rinse systems and heat sink assemblies are not limited to such use or to the rinse systems and heat sink assemblies specifically described therein. They may be used in other rinse systems or other applications requiring a source of dry pressurized air. Likewise, they may be used with other heat sinks or other applications requiring a source of cool air.

The novel heater assemblies and their various components preferably are operated via suitable controllers and operator interface devices. For example, sample temperature sensor 37, heater block temperature sensors 39, condenser block sensor 74, cooler sensors 41, 42, 81, and 82, air pressure sensor 65, moisture sensor 67, vacuum interlock switch 92, and reservoir load sensor 24 may be connected to and provide input to a micro programmable controller. Control panel 13, and other user control or input devices such as touch screens, buttons, switches, and the like, also are preferably connected to the controller, as are additional control switches and the like, so as to activate and control heating elements 35, heat sink cooler 40, condenser cooler 80, air valve 68, drain valve 76, air regulator 64, and solvent feed valve 23 automatically or manually as desired. Additional inputs, such as ambient temperature sensors, and suitable displays and readouts also preferably are provided to allow a user to monitor the status and operation of sample preheater 10.

For example, a user preferably is allowed to input the desired sample temperature which thereafter will be controlled automatically by the controller, for example, via sample temperature sensor 37, heater block temperature sensors 39, cooler sensors 41 and 42, heating elements 35, and heat sink cooler 40. The controller also preferably is programmed to generate alarms and to cut off power to heating elements 35 or to preheater 10 in the event temperature thresholds are exceeded as indicated, e.g. by heater block temperature sensors 39. Rinsing operations, that is, the length of time and rate of solvent flow from the solvent reservoir 20 also may be controlled. A user also preferably is able to set the desired air feed pressure and to set the temperature of condenser block 71. Preferably, the user also will be able to monitor the moisture content of air being fed to solvent reservoir 20. Finally, the controller preferably is programed to utilize the various sensors and control elements to provide diagnostic routines to aid in troubleshooting failures in the various functions and components of preheater 10. The design and implementation of such control programs and functions may be varied as desired.

Heat sink 12 and condenser assembly 70, as well as the various control and interface devices, preferably are mounted in and on a suitable cabinet 16, for example, as shown generally in FIG. 1. It will be appreciated that the heat sink may be operated at relatively high temperatures for extended periods of time. Thus, heat sink 12 preferably is mounted to cabinet 16, as may be seen in FIGS. 5 and 6, via a thermally insulating body 17 interposed between the heat sink and the cabinet. Both cabinet 16 and insulating body 17 have suitable openings which allow direct access to heat sink 12 for introduction of liquid into sample basin 11.

While this invention has been disclosed and discussed primarily in terms of specific embodiments thereof, it is not intended to be limited thereto. Other modifications and embodiments will be apparent to the worker in the art.

What is claimed is:

1. An air feed apparatus for supplying pressurized air, said air feed apparatus comprising:
   (a) a dryer for chilling pressurized air and thereby removing humidity from said pressurized air, which said dryer comprises:
   (b) a condenser assembly comprising:
      i) a condenser block made of metal comprising
         (1) a first part and a second part assembled together on abutting extended surfaces;
         (2) an extended, external planar heat transfer surface on said first part;
         (3) a serpentine passageway, said serpentine passageway (A) extending through said condenser block in a plane generally parallel to said heat transfer surface, (B) being defined by a groove in at least one said abutting surface of said first and second block parts, and (C) having an inlet and an outlet allowing said pressurized air to be introduced into and passed out of said condenser block;

ii) a drain allowing condensed moisture to flow from said passageway; and iii) an active cooling element having a cooling plate mounted to said heat transfer surface of said condenser block for absorbing heat from said condenser block.

2. The air feed apparatus of claim 1, wherein said cooling element is a Peltier cooler mounted to said condenser block.

3. The air feed apparatus of claim 2, wherein said condenser assembly comprises a regulator in fluid communication with said block outlet for reducing the pressure of air discharged from said condenser block.

4. The air feed apparatus of claim 3, wherein said air feed system comprises a moisture sensor adapted to measure the moisture content of air passing through said air feed system.

5. The air feed apparatus of claim 3, wherein said air feed system comprises a moisture sensor upstream of said inlet of said condenser block and a moisture sensor downstream of said outlet of said condenser block.

6. The air feed apparatus of claim 2, wherein said air feed system comprises a moisture sensor adapted to measure the moisture content of air passing through said air feed system.

7. The air feed apparatus of claim 2, wherein said air feed system comprises a moisture sensor adapted to measure the moisture content of air passing through said air feed system.

8. The air feed apparatus of claim 2, wherein said air feed system comprises a moisture sensor upstream of said inlet of said condenser block and a moisture sensor downstream of said outlet of said condenser block.

9. The air feed apparatus of claim 2, wherein said air feed system comprises a moisture sensor upstream of said inlet of said condenser block and a moisture sensor downstream of said outlet of said condenser block.

10. The air feed apparatus of claim 1, wherein said condenser assembly comprises a regulator in fluid communication with said block outlet for reducing the pressure of air discharged from said condenser block.

11. The air feed apparatus of claim 10, wherein said air feed system comprises a moisture sensor adapted to measure the moisture content of air passing through said air feed system.

12. The air feed apparatus of claim 10, wherein said air feed system comprises a moisture sensor upstream of said inlet of said condenser block and a moisture sensor downstream of said outlet of said condenser block.

13. The air feed apparatus of claim 1, wherein said air feed system comprises a moisture sensor adapted to measure the moisture content of air passing through said air feed system.

14. The air feed apparatus of claim 1, wherein said air feed system comprises a moisture sensor adapted to measure the moisture content of air passing through said air feed system.

15. The air feed apparatus of claim 1, wherein said air feed system comprises a moisture sensor upstream of said inlet of said condenser block and a moisture sensor downstream of said outlet of said condenser block.

16. The air feed apparatus of claim 1, wherein said air feed system comprises a moisture sensor upstream of said inlet of said condenser block and a moisture sensor downstream of said outlet of said condenser block.

* * * * *